(12) United States Patent
Chung et al.

(10) Patent No.: US 6,773,902 B1
(45) Date of Patent: Aug. 10, 2004

(54) METHOD FOR PREPARING LYSOPHOSPHATIDYLETHANOLAMINE

(75) Inventors: Guk Hoon Chung, Yongin-si (KR); Young Lae Yang, Suwon-si (KR)

(73) Assignee: Doosan Corporation (KR)

( * ) Notice: Subject to any disclaimer, the term of this patent is extended or adjusted under 35 U.S.C. 154(b) by 165 days.

(21) Appl. No.: 10/031,809

(22) PCT Filed: Nov. 28, 2000

(86) PCT No.: PCT/KR00/01369

§ 371 (c)(1),
(2), (4) Date: Jul. 30, 2002

(87) PCT Pub. No.: WO01/40496

PCT Pub. Date: Jun. 7, 2001

(30) Foreign Application Priority Data

Nov. 30, 1999 (KR) .......................... 1999-53780

(51) Int. Cl.$^7$ ................................. C12P 13/00
(52) U.S. Cl. ...................................... 435/128
(58) Field of Search ......................... 435/128

(56) References Cited

U.S. PATENT DOCUMENTS 5,538,874 A * 7/1996 Hattori et al. ............... 435/128
5,716,814 A * 2/1998 Yesair ......................... 435/134
5,955,327 A * 9/1999 Hirai et al. .................. 435/128
6,268,187 B1 * 7/2001 Chung et al. ............... 435/128

FOREIGN PATENT DOCUMENTS

JP    3123493    3/1991
JP    5003791    1/1993

OTHER PUBLICATIONS

Machine Japanese–English computerized translation publication No. 05–003971 "Preparation of Lysophosphatidylcholine and Lysophosphatidylethanolamine containing linolic acid as oly constituting fatty acid" Toshio et al Pub Date Jan. 14, 1993.*

* cited by examiner

Primary Examiner—Herbert J. Lilling
(74) Attorney, Agent, or Firm—Paul J. Sutton

(57) ABSTRACT

Disclosed herein is a method for purifying the lysophosphatidylethanolamine with high purity by treating the phospholipid mixture with enzymes, followed by solvent fractionaltion without the column purification. The method of the present invention comprises hydrolyzing phospholipid mixture containing 10–99 weight % of phosphatidylethanolamine with phospholipase A2 to produce lysophospholipid; and treating the lysophospholipid with the solvent mixture comprising water and one or more organic solvents selected from the group consisting of low alcohol, hydrocarbon and alkylester to eliminate impurities except lysophosphatidylethanolamine.

12 Claims, No Drawings

METHOD FOR PREPARING LYSOPHOSPHATIDYLETHANOLAMINE

BACKGROUND OF THE INVENTION

1. Field of the Invention

The present invention relates to a method for preparing lysophosphatidylethanolamine from phospholipid mixture with a high purity. More specifically, the present invention relates to a method for purifying lysophosphatidylethanolamine with a high purity by treating phospholipid mixture with enzyme then applying solvent fractionation, without column purification.

2. Description of the Prior Art

Lysophosphatidylethanolamine exists naturally in animal cells or plant cells, and is plentiful in egg yolk or brain cell. The lysophosphatidylethanolamine is derived from phosphatidylethanolamine, which is a kind of phospholipids and detected in cell membrane. Phosphatidyletlanolamine, rich in egg yolk or soybean lecithin, is a kind of phospholipid containing two fatty acids in its molecule. In organisms, when Phospholipase A2, a kind of phospholipid hydrolase, acts on phosphatidylethanolamine, one fatty acid of which positioned in the sn-2 site is eliminated to produce lysophosphatidylethanolamine.

Lysophosphatidylethanolamine is known as playing an important role in the ripeness and senescence of fruit. It is well known that treating tomato plant with lysophosphatidylethanolamine suppresses senescence of their leaves and fruit, and that treating harvested tomato with lysophosphatidylethanolamine extends their storage term (U.S. Pat. Nos. 5,110,341, 5,126,155). It is also known that treating an apple with lysophosphatidylethanolamine promotes the formation of anthocyanin in the skin of the apple, and suppresses the loss of firmness when storing. Further, it is known that the above-described effects relate to the function of the lysophosphatidylethanolamine such as reducing the respiration rate of fruit(for example, apple, cranberry, tomato, etc.) and promoting or suppressing the formation of ethylene gas (Farag. K. M. and J. P. Palta, "Stimulation of Ethylene Production by Erea, Thidiazoron, and Lysophosphatidylethanolamine and Possible sites of this stimulation" Annual meeting of the American Society of Plant Physiologists, April 1989).

The method of treating with lysophosphatidylethanolamine solution, which is controlled to have an appropriate concentration, has been used to prolong the life of the cut flowers (Hort Science 32(5): 888–890, 1997). Recently, silver thiosulfate solution, generally containing sugar, has been used for the purpose of suppressing the senescence of flowers by the method of treating the harvested (cut) flowers with the solution for 20 hours or more. The above solution, however, has the drawback that silver ion contained therein causes environmental pollutions. Because lysophosphatidylethanolamine purified from the nature, like the silver thiosulfate solution, has a characteristic of increasing the shelf life of the cut flower in a vase, lysophosphatidylethanolamine has been a target of wide investigation in this field.

Until now, the industrial method for producing lysophosphatidylethanolamine with high purity has not been developed. Just a small scale of isolation and purification of the lysophosphatidylethanolamine, using silica gel column chromatography, was performed in the laboratories. A little amount of lysophosphatidylethanolamine, just as for a reagent, is sold by Avanti Polar Lipids, Inc. or by Sigma Chemical Co., in a high price. Furthermore, when lysophosphatidylethanolamine is prepared by column chromatography, because lysophosphatidylcholin and lysophosphatidylethanolamine have similar patterns of migration, it is very difficult to isolate lysophosphatidylethanolamine from the two. When performing column chromatography, using a low-toxic organic solvent such as hexane or ethanol as a single solvent, because the solubility of the lysophosphatidylethanolamine to the solvent is very low, it is very difficult to purify lysophosphatidylethanolamine. Meanwhile, when chromatography is performed with using the solvent which is known as having a high toxicity (for example, chloroform, benzene or methanol), the result of the purification is good but the yield is low and the purification cost is high.

SUMMARY OF THE INVENTION

Thus, an object of the present invention is to provide a method for preparing lysophosphatidylethanolamine, with a high purity.

To accomplish the above object the present invention provides a method for preparing lysophosphatidylethanolamine comprising the steps of; treating phospholipid mixture comprising phosphatidylethanolamine with phospholipase to convert said phosphatidylethanolamine into the lysophosphatidylethanolamine; treating above-obtained lysophospholipid mixture comprising the lysophosphatidylethanolamine with a specific solvent mixture to extract and crystallize the lysophosphatidylethanolamine selectively; and recovering the lysophosphatidylethanolamine.

The present invention also provides a method further comprising the step of treating phosphatidylcholine, which is plentiful in the phospholipid, with phospholipase D, a kind of phospholipid hydrolyzing enzyme, to magnify the content of phosphatidylethanolamine in phospholipid mixture.

These and other features of the present invention will be well understood by one skilled in the art from the following detailed descriptions.

DETAILED EXPLANATION OF THE INVENTION

The present invention will be described in detail hereinafter.

The start material used in the method of the present invention is the phospholipid mixture containing 10–99 weight % of phosphatidylethanolamine, preferably 30–99 weight % of phosphatidylethanolamine. The examples of such mixture are soybean lecithin, crude soybean lecithin, yolk lecithin, and so on.

However, the content of phosphatidylethanolamine contained in the phospholipid mixture that exists in nature is less than the content of the phosphatidylcholine. For more efficient process, it is necessary to increase the content of phosphatidylethanolamine in the phospholipid.

For example, crude soybean lecithin ("crude lecithin"), a by-product of a process for preparing soybean oil, is composed of 60–70% of polar lipid (phospholipid/glycolipid), 27–39% of soybean oil, 1–3% of water, 0.5–3% of other components. The polar lipid is purified by removing the soybean oil(a kind of neutral oil) contained in crude lecithin. The composition of the polar lipid in the purified state is as follows; 22–30% of phosphatidylcholine ("PC"); 2–5% of lysophosphatidylcholine ("LPC"); 16–22% of phosphatidylethanolamine ("PE"); 0.5–2% of lysophosphatidylethanolamine ("LPE"); 0.5–8% of phosphatidic acid ("PA");

0.1–3% of phosphatidylserine; 6–15% of phosphatidylinositol, etc. Egg yolk lecithin is composed of 73–83% of PC, 2–5% of LPC, 13–17% of PE, 0.1–3% of LPE, and other remnants. Since phospholipid contains very small quantity of lysophosphatidylethanolamine, it is next to impossible to commercially use lysophosphatidylethanolamine by directly purifying it from the above lecithins.

Therefore, it is desirable to prepare the start material as follows; after converting PC, plentifully contained in the phospholipid mixture, into PE, then purifying PE from the phospholipid mixture or increasing PE by such a method as concentration is followed when needed. The method of increasing PE content includes solvent fractionation using different solubility of phospholipids to various solvents, fractionation by column chromatography, concentration of phosphatidylethanolamine using phospholipid-converting enzyme, and so on.

As a method for concentrating phosphatidylethanolamine by column chromatography, fractionation and concentration method using the adsorbent such as silica gel or Florisil, or the ion-exchange resin such as DEAE cellulose or TEAE cellulose is widely known [G. Rouser, G. Krichevsky, A. Yamanoto, "Lipid Chromatographic Analysis" ed by G. V. Marinetti, Vol.1, p99, Dekker, New York (1967), D. J. Hanahan, J. C Dittmer, E. Warashina, J. Biol. Chem. 228, 685(1957)]. As the methods of fractionation using the difference of the solubility, a fractionation using alcohol [V. H. Pardon, Fette Seifen Anstrichmittel 86, 55(1984), J. Holzl and H. Wangner, Z. Naturforsch., 26b, 1151(1971)] and centrifugal partition chromatography[Bio Industry 2(8) 40 (1985)] are known.

As another method for increasing phosphatidylethanolamine content in the phospholipid, enzyme (specifically, phospholipase D or phosphatidylcholine phosphatidohydrolase, E.C.3.1.1.4.) can be used. Phospholipids consists of a sn-glycerol-3-phosphate backbone and fatty acyl chains on the hydroxyl groups at carbons 1 and 2. Phospholipase A1 and A2 catalyzes the hydrolysis of sn-1 and sn-2 acyl group, respectively. Phospholipase C hydrolyzes the phosphodiester bond on the side of glycerol backbon. Phospholipids are classified according to the headgroup substituent on the phosphate group and this head group such as choline or ethanolamine can be hydrolyzed by phospholipase D. Phospholipase D is useful for the production of many kinds of phosphatidic acid derivatives due to its hydrolysis activity and transphosphatidylation activity. When phospholipid converting enzyme (namely phospholipase D) and an appropriate amount of ethanolamine are added to phospholipid of soybean or egg yolk, phospholipid containing a large quantity of phosphatidylethanolamine is obtained by a transphosphatidylation reaction[S. F. Yang, et al., J. Biol. Chem., 242(3), 477–484(1967). R. M. C. Dawson, Biochem. J., 102 205–210(1967)].

Therefore, such phospholipid mixture prepared by the above-known method that contains phosphatidylethanolamine in high concentration can be used as the start material of the present invention.

In the example of the present invention, for the purpose of increasing phosphatidylethanolamine content in the phospholipid, phospholipase D(a kind of phospholipid convertase) is used, which enzyme can be prepared from microorganism or plant. A general method for obtaining phospholipase D from cabbage is disclosed by Yang et al.[S. F. Yang, et al., J. Biol. Chem.; 242(3), 477–484(1967)]. And the phospholipase D extracted from peanut seeds, cotton seeds, soybean and so on can be used in the present invention, with partially or completely purified states. As the phospholipase D produced from the microorganism, such as the Streptomyces genus-derived enzyme produced by fermentation reaction can be used. Generally, in the converting reaction, phospholipase D produced by the microorganism is more preferable than that extracted from plant because they have better efficiency in the reaction of converting phospholipid.

This reaction of converting enzyme can be carried out under general conditions. The mixture obtained from the above-reaction can be applied in the following hydrolysis reaction, or purified for the following use.

According to the present invention, by treating the phospholipid mixture whether it is preliminary treated with phospholipase D or not, with such phospholipid hydrolase as phospholipase A2, the phosphatidylethanolamine in the mixture is converted to lysophosphatidylethanolamine. As a result, it is possible to obtain a large quantity of lysophosphatidylethanolamine.

Phospholipid hydrolase that can be used in the present invention includes phospholipase A2 extracted from bovine or porcine pancreas, lipase having the activity of phospholipase A2, and pancreatin of bovine or porcine pancreas having inactivated protease and lipase. It also includes phospholipase A2 produced from fermentation of the microorganism. Phospholipase A2 is the enzyme that hydrolyzes the ester bondings between glycerol and fatty acid in the sn-2 site of the phospholipid, which is prevalent in snake venom or pancreas of animals. For industrial purposes, phospholipase A2 extracted from porcine pancreas then concentrated is on sale. The phospholipase A2 used in an Example of the present invention is the one extracted and purified from porcine pancreas, which is the product of Novo Nordisk A/S developed for commercial use.

Generally, the enzymatic hydrolysis reaction of phospholipid comprises the steps of dissolving phospholipid or mixture of phospholipid in water or organic solvents having 5–100 times larger volume, adding the enzyme thereto, and stirring vigorously at a constant temperature. The temperature of the enzyme reaction is controlled to be moderate, namely, room temperature to 70° C. preferably 25–50° C.

In case of using an organic solvent in the enzyme reaction, it is preferable to consider the boiling point and the flash point of the solvent for the stability of the process and operation. The amount of enzyme added is determined considering the sort, purity, the state of material, price, and the content of phospholipid in substrate, etc. Generally, the amount of the enzyme used per 1 kg of phospholipid is 10,000–50,000 units(Lecitase, the content recommended by Novo Nordisk A/S). The reaction time of the hydrolysis is determined by the content of enzyme added, reaction temperature, phospholipid content, the rate of stirring and so on. The enzyme reaction of the present invention is carried out by the reaction method recommended by the company supplying the enzyme, except that the content of enzyme and the reaction temperature are controlled for a constant hydrolytic reaction, and that organic solvent is added for the solubilization of phospholipid.

The organic solvent for the enzymatic reaction includes diethyl ether, isopropyl ether, butyl ether, n-hexane, cyclohexane, n-heptane, methyl acetate, ethyl acetate, butyl acetate, and so on.

Water and organic solvent remaining after the enzymatic reaction, if needed, can be used for the following organic solvent fractionation process, without removing them. Specifically, water is needed in the following organic solvent fractionation process. Therefore, in the below-described organic solvent fractionation process, the water that is remained in enzymatic reaction of hydrolysis is used or additional water is added.

Meanwhile, although the enzymatic phospholipid conversion reaction is performed, it is hard to expect a 100% conversion yield and it is impossible to avoid producing by-products such as phosphatidic acid (PA), lysophosphatidic acid, etc. Since lysophospholipid prepared from the enzymatic reaction is highly hydrophilic in their interface, it is difficult to recover lysophospholipid completely. When lysophospholipid is recovered by solvent extraction, the concentrating process is difficult because of high percentage of water, which produces bubbles in the evaporation step. Thus, after producing the lysophospholipid, it is not easy to isolate lysophosphatidylethanolamine from the lysophospholipid selectively. Since lysophosphatidylethanolamine and lysophosphatidylcholine, the primary component of the lysophospholipid, are similar in solubilities to the organic solvent, the isolation step is difficult.

To solve these problems and to obtain a highly pure lysophosphatidylethanolamine, the present invention provides a method comprising treating the above LPE-containing lysophospholipid mixture with the mixture of water and one or more organic solvent selected from the group consisting of low alcohol, hydrocarbon, alkyl ester, and so on, then crystallizing the resultant mixture. As the result, the present invention provides a method that can eliminate the impurities [i.e., phospholipid (for example, PC, LPC, PE, PA, etc.), neutral lipid, fatty acid, cholesterol, and so on, all of which are produced after reaction] except lysophosphatidylethanolamine, and thus can produce a highly pure lysophosphatidylethanolamine.

To remove the impurities from the reaction mixture except lysophosphatidylethanolamine, the solvent used in the fractionation process of the present invention is the mixture of water and one or more organic solvents selected from the group consisting of low alcohols with 1–4 carbons (for example methanol, ethanol, propanol, isopropanol, butanol, etc); one or more hydrocarbons(aliphatic hydrocarbon with 6–12 canbons, for example pentane, hexane, cyclohexane, heptane, octane, cyclooctane, methylcyclohexane, etc); and alkyl ester of carboxylic acid (for example, methyl acetate, ethyl acetate, methyl propionate, methyl butylate, methyl caproate, etc., having 2–6 carbons).

In the step of solvent fractionation, a total amount of solvent used is in the range of 0.5–20 times the weight of phospholipid, preferably 5–10 times the weight of phospholipid.

The organic solvents preferably used in the present invention are, for example, methanol or ethanol as a low alcohol, hexane, cyclohexane or heptane as a hydrocarbon, and ethyl acetate as an alkyl ester.

The desirable volume ratio of the mixture of water and organic solvent is in the range of 0.5–80:20–99.5. As described above, when water or organic solvent used in the step of hydrolysis reaction is remained, above described preferred range can be accomplished in solvent fractionation step, by adding additional appropriate amount of water or organic, or not. In case of using two or more kinds of organic solvents, the ratio is not restricted specifically. In case of using the mixture of organic solvent containing low alcohol, the low alcohol can be contained with 10–99 volume %.

After treating the resultant reaction mixture of phospholipid hydrolysis with the solvent mixture of organic solvent and water, lysophosphatidylethanolamine with a high purity is obtained by the following steps of; crystallizing the mixture in the low temperature ranged −10° C. to 50° C. removing the impurities by centrifugation, and filtrating or decanting the supernatant. The crystallization step can be carried out by controlling the temperature, separately after the step of solvent fractionation, or can be carried out simultaneously with the step of the solvent fractionation.

In the present invention, the reaction temperature for solvent fractionation of the phospholipid is one of the most important factors. The solubilities of lysophosphatidylethanolamine and lysophosphatidylcholine to the organic solvent are both dependent on the temperature, much. Temperature for more selective fractionation of lysophospholipid should be controlled in a moderate condition of −10° C. to 50° C. preferably −10° C. to 30° C. more preferably −5° C. to 6° C.

In the present invention, it is very important to control the pH of the reaction for more efficient fractionation. In the present invention, the preferable pH of the reaction is pH 3–9, and more preferably pH 4–8.

LPE crystal produced from the step of organic solvent fractionation and the step of the crystallization can be recovered by a conventional method, for example, filtration, centrifugation, decantation of supernatant and so on.

The procedure comprising the steps of organic solvent fractionation, crystallization, and recovery of crystal can be carried out once. To enhance of the purity of LPE, the procedure can be carried out twice or more times, wherein the sort and mixture ratio of the organic solvents used in each procedure can be the same or different.

The process of preparing lysophosphatidylethanolamine according to the present invention can be applied to a lab scale or an industrial scale, and the lysophosphatidylethanolamine can be prepared efficiently without any additional difficulties. Such a high purity lysophosphatidylethanolamine prepared with a low price can be used broadly in pharmaceuticals or agriculture.

PREFERRED EMBODIMENT OF THE INVENTION

The present invention will be embodied by way of the following examples. However, these examples are provided for the purpose of illustration only, and should not be construed as limiting the scope of the invention, which is properly delineated in the accompanying claims.

EXAMPLE 1

80 g of purified phospholipid of egg yolk(made in Doosan Serdary Research Labs, phosphatidylcholine 75%, phosphatidylethanolamine 14%, others 11%; wherein % is weight %) is dissolved in 80 ml of chloroform. 450 g of silica gel (Merck, 70–230 mesh) is added to 1,000 ml of chloroform, and the mixture is filled in 70 mm×700 mm of glass column. After injecting above-dissolved phospholipid solution into the column, the column is eluted with 500 ml of chloroform, 1,000 ml of chloroform:methanol(≈95:5, v/v) mixture, 1,500 ml of chloroform:methanol(≈90:10, v/v) mixture, 2,000 ml of chloroform:methanol(≈85:15, v/v) mixture, then, the eluted phospholipid is examined by thin layer chromatography. The fractions that phosphatidylethanolamine is eluted are collected, then concentrated with rotary vacuum evaporator at 50° C. The phosphatidylethanolamine obtained from the above process is analyzed by HPLC(Shimazu, Japan). As a result, 18.5 g of phosphatidylethanolamine with 76% of purity (containing 11% of phosphatidylcholine) is obtained.

15 g of the above-obtained phosphatidylethanolamine (containing 11% of phosphatidylcholine) is dissolved in 150 ml of diethyl ether, then 20 ml of sodium acetate buffer solution(pH 5.6, 100 mM) containing 100 mM $CaCl_2$ is added thereto. 5 ml of Lecitase (10,000 IU/ml, made in Novo Nordisk A/S) is added to the solution, then the solution is vigorously stirred at 30° C. for 13 hours. After stationing the solution, the solvent and the produced fatty acid are eliminated by decanting supernatant. The precipitate is extracted with 200 ml of hexane:ethanol:water(≈1:1:0.3, v/v/v) solution at room temperature. After eliminating the lower water layer of the solution, 50 ml of ethanol is added to the remainder, and the resultant is filtrated at room temperature. The filter cake is again treated with 100 ml of hexane:ethanol(≈1:1, v/v) solution, and filtrated, then dried. By analyzing the resultant dried substance with liquid chromatography, it is found that 4.5 g of lysophosphatidylethanolamine with 98% of purity is obtained.

EXAMPLE 2

4 g of phosphatidylethanolamine with 99% of purity (made in Doosan Serdary Research Labs.) is dissolved in 50 ml of ethylacetate, then 50 ml of sodium acetate buffer solution(pH 5.6, 100 mM) containing 100 mM of $CaCl_2$ is added thereto. 1 ml of Lecitase(Novo Nordisk A/S) is added to above solution, then the solution is vigorously stirred at 30° C. for 6 hours. After stationing the solution at room temperature for 1 hour, the solvent and the produced fatty acid are eliminated by decanting supernatant. The precipitate is extracted with 20 ml of hexane:ethanol:water (≈1:1:0.3, v/v/v) mixture. After eliminating the lower water layer of the solution, 5 ml of ethanol is added to the remainder, and the resultant is left at −5° C. for 3 hours, then filtrated. The filter cake is treated with 15 ml of hexane:ethanol(≈1:1, v/v) solution, and filtrated, then dried. By analyzing the resultant dried substance using the liquid chromatography, it is found that 0.85 g of lysophosphatidylethanolamine with a purity of 98% is obtained.

EXAMPLE 3

100 g of purified phospholipid of egg yolk, DS-PL95E (made in Doosan Serdary Research Labs, phosphatidylcholine 75%, phosphatidylethanolamine 14%, others 11%) is dissolved in 500 ml of ethylacetate. 8,000 unit of cabbage phopholipase D prepared by the method of Yang [S. F. Yang, et al., J. Biol. Chem., 242(3), 477–484(1967)] is mixed with 500 ml of sodium acetate buffer solution(100 mM, pH 5.6) containing 80 mM of $CaCl_2$ and 25 g of ethanolamine, then the mixture is mixed with the above-dissolved phospholipid solution, and followed by reacting it at room temperature for 13 hours while stirring with 300 rpm. By analyzing the resultant compound with HPLC, it is found that the content of phosphatidylethanolamine is 62% and the content of phosphatidylcholine is 22% in the reaction solution. 500 ml of the reaction solution is taken and used as start material for the Example 4.

10 ml of Lecitase(10,000 IU/ml, Novo Nordisk A/S) is added to 500 ml of the reaction solution, then the solution is vigorously stirred at 30° C. for 6 hours. After stationing the solution for 5 hours, the solvent and the produced fatty acid is eliminated by decanting the supernatant. The remaining reaction solution is extracted with 1,000 ml of the hexane:ethanol (≈1:1, v/v) mixture at room temperature. After eliminating the supernatant, 200 ml of ethanol is added to the remaining solution, and the resultant is stored at 4° C. for 12 hours. Then by filtrating the resultant solution, filter cake is recovered. The recovered cake is treated with 200 ml of the hexane:ethanol:water (≈1:1:0.3, v/v/v) solution, and filtrated, then stationed for 1 hour. After eliminating the lower water layer, 100 ml of ethanol is added to the remainder, then filtration is performed. The filter cake is treated with 200 ml of the hexane:ethanol (≈1:1, v/v) solution, and stored at 4° C. for 8 hours. Filtration and drying is followed. By analyzing the resultant dried substance, it is found that 10.7 g lysophosphatidylethanolamine, with a purity of 99% is obtained.

EXAMPLE 4

5 ml of Lecitase(10,000 IU/ml, Novo Nordisk A/S) is added to 500 ml of the solution prepared from Example 3, then the mixture is vigorously stirred at 30° C. for 10 hours. After stationing the solution, the solvent and the produced fatty acid are eliminated by decanting supernatant. The remaining solution is extracted with 1,000 ml of the hexane:ethanol:water(≈1:1:0.3, v/v/v) mixture. After eliminating the supernatant (i.e., the hexane layer) 200 ml of methanol is added thereto, and the resultant is left for 2 hours then filtrated. The filter cake is treated with 200 ml of hexane:methanol:water (≈1:1:0.3, v/v/v) solution. The resultant is stationed for 2 hours, and filtrated, then dried in vacuum at 60° C. By analyzing the resultant dried substance using the liquid chromatography, it is found that 8.5 g of lysophosphatidylethanolamine with a purity of 98% is obtained.

EXAMPLE 5

10 g of dipalmitoylphosphatidylcholine(made in Doosan Serdary Research Labs, phosphatidylcholine 99%) is dissolved in 500 ml of diethylether 500 unit of phopholipase D derived from Streptomyces spp. (Sigma Chemical Co.) is mixed with 500 ml of sodium acetate buffer (100 mM, pH 5.6) containing 80 mM of $CaCl_2$ and 6 g of ethanolamine, then the mixture is mixed with the above-dissolved phospholipid solution. The mixture is reacted for 48 hours while stirring with 300 rpm at the room temperature. By analyzing the resultant with HPLC, it is found that the content of dipalmitoylphosphatidylethanolamine is 82% and the content of dipalmitoylphosphatidylcholine is 16% in the phospholipid of the reaction solution. 5 ml of Lecitase (10,000 IU/ml, Novo Nordisk A/S) is added to the reaction solution then the solution is stirred vigorously at 30° C. for 10 hours. After extracting the solution with 300 ml of chloroform:methanol (2:1, v/v) mixture, the lower chloroform layer is concentrated at 50° C. by rotary vacuum evaporator to eliminate the solvent. As a result, 8.2 g of concentrated material is obtained. The concentrated material is dissolved in 100 ml of hexane ethanol (−1:1, v/v) mixture while heating, and 60 ml of water is added thereto. After eliminating the lower water layer, 50 ml of ethanol is added thereto and the resultant is stored at −8° C. for 4 hours then filtrated. The filter cake is treated with 100 ml of the hexane:ethanol (≈1:1, v/v) solution, and the resultant is filtrated then dried. The above process is repeated twice. By analyzing the resultant dried substance by liquid chromatography, it is found that 3.5 g of lysophosphatidylethanolamine with a purity of 97% is obtained.

EXAMPLE 6

5 g of soybean phospholipid, i.e. Phospholipon 90G(made in Natterman Phospholipid GMBH, phosphatidylcholine 94%, lysophosphatidlycholine 2%, others 4%) is dissolved in 100 ml of diethylether. 40 unit of phopholipase D derived from Streptomyces spp. (Sigma Chemical Co.) is mixed with 100 ml of sodium acetate buffer (100 mM, pH 5.6) containing 40 mM of $CaCl_2$ and 2.4 g of ethanolamine, then the mixture is mixed with the above-dissolved phospholipid solution. The mixture is reacted for 36 hours while stirring with 300 rpm at room temperature. By analyzing the resultant with HPLC, it is found that the content of phosphatidylethanolamine is 72% and the content of phosphatidylcholine is 18.3% in the phospholipid the reaction solution.

2 ml of Lecitase (10,000 IU/ml, Novo Nordisk A/S) is added to the reaction solution, then the solution is vigorously stirred at 30° C. for 5 hours. After the extracting the solution with 300 ml of chloroform:methanol (2:1, v/v) mixture, the lower chloroform layer is concentrated by rotary vacuum evaporator at 50° C. then 4.5 g of the resultant is obtained. The resultant is precipitated by 80 ml of cold acetone twice, then acetone-insoluble material is obtained. The resultant material is dissolved in 50 ml of the hexane:ethanol ($\approx$9:1, v/v) mixture while heating, then 15 ml of water is added thereto. After stationing for 2 hours, the lower water layer is eliminated, and 50 ml of ethanol is added thereto. The resultant mixture is stored at −8° C. for 4 hours, then filtrated at −8° C. The filter cake is again treated with 100 ml of the hexane:ethanol ($\approx$1:1, v/v) solution, then the resultant is filtrated and dried. The above process is repeated twice. By analyzing the resultant dried substance with liquid chromatography, it is found that 0.9 g lysophosphatidylethanolamine with a purity of 86% is obtained.

EXAMPLE 7

30 g of purified phospholipid of egg yolk, DS-PL95E (made in Doosan Serdary Research Labs, phosphatidylcholine 75%, phosphatidylethanolamine 14%, others 11%) is dissolved in 60 ml of ethylacetate. 800 unit of phopholipase D derived from Streptomyces spp. (Sigma Chemical Co.) is mixed with 100 ml of sodium acetate buffer solution (100 mM, pH 5.6) containing 80 mM of $CaCl_2$ and 8 g of ethanolamine, then the mixture is mixed with the above-dissolved phospholipid solution. The mixture is reacted for 13 hours while stirring with 300 rpm at 35° C. By analyzing the resultant with HPLC, it is found that the content of phosphatidylethanolamine is 79% and the content of phosphatidylcholine is 16% in the phospholipid of the reaction solution. 3 ml of Lecitase (10,000 IU/ml, made in Novo Nordisk A/S) is added to the reaction solution, then the mixture is vigorously stirred at 35° C. for 6 hours. 50 ml out of the reaction solution is treated with 100 ml of anhydrous ethanol, and the resultant is left at −2° C. for 30 minutes, then filtrated. 50 ml of 80% ethanol is added to the resultant 5.7 g of filter cake, then stirred at 300 rpm for 30 minutes. The resultant is stored at −2° C. for 4 hours and filtrated. Using 50 ml of 80% ethanol, the above process is repeated twice, then the filter cake is dried. By analyzing the resultant dried substance with liquid chromatography, it is found that 1.5 g of lysophosphatidylethanolamine with a purity of 97% is obtained.

EXAMPLE 8

50 ml out of the reaction solution prepared from Example 7 is concentrated at 40° C. by rotary vacuum evaporator to eliminate the solvent, i.e. ethylacetate, then the same process as the Example 7 is performed. By analyzing the resultant dried substance with liquid chromatography, it is found that 1.9 g of lysophosphatidylethanolamine with a purity of 95% or more is obtained.

EXAMPLE 9

50 ml out of the reaction solution prepared from Example 7 is placed in the round-bottomed flask, and concentrated at 40° C. by rotary vacuum evaporator to eliminate the solvent, i.e. ethylacetate. The resultant is treated with 100 ml of anhydrous ethanol, and left at −2° C. for one and half hours, then followed by filtration. 8.9 g of the filter cake is treated with 100 ml of ethanol:ethylacetate:water (=1:0.5:0.5, v/v/v) mixture, and the resultant is heated for 30 minutes while slowly stirring. Then, the resultant solution is filtrated to eliminate the impurities, and the remaining solution is cold-stored at −2° C. for 3 hours. The crystallized solution is filtrated to obtain 4.8 g of filter cake. The filter cake is treated with 80 ml of ethanol:ethylacetate:water (=1:0.5:0.5, v/v/v) mixture, and heated for 30 minutes while slowly stirring at 60° C. Then the solution mixture is slowly cooled to the temperature of −2° C. and filtrated. The filter cake is treated twice with the same method as described above, and the resultant is dried in vacuum at 30° C. By analyzing the dried resultant substance with liquid chromatography, it is found that 1.6 g of lysophosphatidylethanolamine with a purity of 97% is obtained.

Comparative Example 1

10 ml out of the reaction solution prepared from Example 7 is treated with 50 ml of the chloroform:methanol ($\approx$2:1, v/v) mixture for extraction. After eliminating the upper water and methanol layer, 10 ml of ethanol(or methanol) is added to the lower layer, and the resultant is left at −5° C. for 1–3 hours. By analyzing the resultant, it is found that the crystallized lysophosphatidylethanolamine is not produced at all, but there is only a mixture of lysophosphatidylethanolamine, lysophosphatidylcholine, fatty acids, phosphatidylcholine, sphingomyelin, phosphatidylethanolamine, as the reaction resultant, in the lower layer.

Comparative Example 2

10 ml out of the reaction solution prepared from Example 7 is treated with 30 ml of chloroform for extraction. Centrifugation is performed at 2,000 rpm for 5 minutes to eliminate the upper water layer. By analyzing the lower layer by thin layer chromatography (TLC), it is found that the crystallized lysophosphatidylethanolamine is not produced at all, but there is only a mixture of lysophosphatidylethanolamine, lysophosphatidylcholine, fatty acids, phosphatidylcholine, sphingomyelin, phosphatidylethanolamine, as the reaction resultant, in the lower layer.

Comparative Example 3

10 ml out of the reaction solution prepared from Example 7 is treated with 30 ml of ethyl acetate (or hexane) for extraction. Centrifugation is performed at 2,000 rpm for 5 minutes. By analyzing the upper layer by thin layer chromatography (TLC), it is found that the crystallized lysophosphatidylethanolamine is not produced at all, but there is only a mixture of lysophosphatidylethanolamine, lysophosphatidylcholine, fatty acids, phosphatidylcholine, sphingomyelin, phosphatidylethanolamine, as the reaction resultant, in the lower layer.

A high purity of lysophosphatidylethanolamine prepared according to the method of the present invention, as described above, is produced with low cost and can be used in the field of food, medicine, cosmetics, and agriculture.

What is claimed is:

1. A method for preparing lysophosphatidylethanolamine with high purity comprising the steps of:

(1) obtaining lysophospholipid by treating phospholipid mixture comprising phosphatidylethanolamine with phospholipid hydrolase to convert said phosphatidylethanolamine into lysophosphatidylethanolamine;

(2) extracting the said lysophospholipid with a solvent mixture comprising water and one or more organic solvent selected from the group consisting of low alcohol; hydrocarbon; and alkylester;

(3) precipitating the crystallized lysophosphatidylethanolamine by stationing the reaction mixture obtained from step (2) at $-10°$ C.$-50°$ C.; and (4) recovering the precipitate produced from step (3).

2. The method according to claim 1, wherein said phospholipid mixture of step (1) contains phosphatidylethanolamine in an amount of 10 to 99% by weight.

3. The method according to claim 2, wherein said phospholipid mixture contains phosphatidylethanolamine in an amount of 30 to 99% by weight.

4. The method according to claim 1, wherein said phospholipid mixture of step (1) is soybean phospholipid or egg yolk phospholipid.

5. The method according to claim 1, wherein said phospholipid mixture of step (1) is treated with phospholipid convertase, under the condition that ethanol amine is added, then said phosphatidylcholine of the mixture is converted to phosphatidylethanolamine.

6. The method according to claim 1, wherein the phospholipid hydrolase of step (1) is phospholipase A2.

7. The method according to claim 1, wherein the organic solvent of step (2) is a mixture of two or more solvent selected from the group consisting of low alcohol with 1 to 4 carbons; alphatic or aromatic hydrocarbon having 6–12 carbons with straight or branched; and ester composed of a straight or branched fatty acid with 2 to 6 carbons and a straight or branched alkyl group.

8. The method according to claim 7, wherein said alcohol is methanol or ethanol, said hydrocarbon is hexane, cyclohexane or heptane, and said alkyl ester is ethyl ester.

9. The method according to claim 1, wherein the step (2) and step (3) are performed at the same time.

10. The method according to claim 1, wherein crystallization of the step (3) is performed at $-10°$ C.$-30°$ C.

11. The method according to claim 1, 7 or 8, wherein the solution mixture of step (2) comprises water and organic solvent with ratio of 0.5–80:20–99.5 by volume %.

12. The method according to claim 1, wherein the solvent mixture of step (2) is the mixture of water and alcohol.

* * * * *